US010064893B2

(12) United States Patent
Contag et al.

(10) Patent No.: US 10,064,893 B2
(45) Date of Patent: *Sep. 4, 2018

(54) IMMUNE EFFECTOR CELLS PRE-INFECTED WITH ONCOLYTIC VIRUS

(71) Applicant: The Board of Trustees of the Leland Stanford Junior University, Stanford, CA (US)

(72) Inventors: Christopher H. Contag, Stanford, CA (US); Stephen H. Thorne, Pittsburgh, PA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/792,424

(22) Filed: Jul. 6, 2015

(65) Prior Publication Data
US 2015/0320800 A1 Nov. 12, 2015

Related U.S. Application Data

(63) Continuation of application No. 13/470,558, filed on May 14, 2012, now Pat. No. 9,101,658, which is a continuation of application No. 11/529,807, filed on Sep. 29, 2006, now abandoned.

(60) Provisional application No. 60/722,799, filed on Sep. 30, 2005.

(51) Int. Cl.
*A61K 35/17* (2015.01)
*C12N 5/0783* (2010.01)
*A61K 39/00* (2006.01)
*A61K 48/00* (2006.01)
*A61K 35/12* (2015.01)
*A61K 35/13* (2015.01)

(52) U.S. Cl.
CPC .......... *A61K 35/17* (2013.01); *A61K 39/0011* (2013.01); *A61K 48/00* (2013.01); *C12N 5/0636* (2013.01); *C12N 5/0638* (2013.01); *C12N 5/0646* (2013.01); *A61K 35/13* (2013.01); *A61K 2035/124* (2013.01); *A61K 2039/5156* (2013.01); *A61K 2039/5158* (2013.01); *C12N 2710/24132* (2013.01)

(58) Field of Classification Search
CPC ...... A61K 2039/5154; A61K 2039/525; A61K 2039/548; A61K 2039/58; C12N 2710/24111; C12N 2710/24132
See application file for complete search history.

(56) References Cited

U.S. PATENT DOCUMENTS 9,101,658 B2 * 8/2015 Contag .............. A61K 39/0011
2002/0031498 A1 3/2002 Smith et al.
2002/0034819 A1 * 3/2002 Smith .................. A61K 35/15
435/366
2003/0077819 A1 * 4/2003 Groene ................ A61K 35/19
435/325
2005/0031643 A1 * 2/2005 Szalay ................. A61K 35/74
424/199.1

FOREIGN PATENT DOCUMENTS

WO 99/45783 9/1999
WO 00/73479 12/2000

OTHER PUBLICATIONS

Wheelock, PNAS 48:1358-1366, 1962.*
Chester et al, Nature Biotechnology 20:256-263, 2002.*
Leemhuis et al, Biol. Blood Marrow Trans. 11:181-187, 2005.*
McCart et al, Cancer Res. 61:8751-8757, 2001.*
Sanchez-Puig et al, Virol. J. 1:10-17, 2004.*
Thorne and Kirn, Expert Op. Biol. Ther. 4(8):1307-1321, 2004.*
Chester; et al., "Tumor antigen-specific induction of transcriptionally targeted retroviral vectors from chimeric immune receptor-modified T cells", Nature Biotechnology (Mar. 2002), 20(3):256-63.
Hamerman; et al., "NK cells in innate immunity", Current Opinion in Immunology (Feb. 2005), 17(1):29-35.
Kirn; et al., "Replication-selective virotherapy for cancer: Biological principles, risk management and future directions", Nature Medicine (Jul. 2001), 7(7):781-7.
Leemhuis; et al., "A phase I trial of autologous cytokine-induced killer cells for the treatment of relapsed Hodgkin disease and non-Hodgkin lymphoma", Biology of Blood and Marrow Transplantation (Mar. 2005), 11:181-187.
Lu; et al., "A novel population of expanded human CD3+CD56+ cells derived from T cells with potent in vivo antitumor activity in mice with severe combined immunodeficiency", The Journal of Immunology (Aug. 1994), 153(3):1687-96.
McCart; et al., "Systemic cancer therapy with a tumor-selective vaccinia virus mutant lacking thymidine kinase and vaccinia growth factor genes", Cancer Research (Dec. 2001), 61(24):8751-7.
Puhlmann; et al., "Vaccinia as a vector for tumor-directed gene therapy: biodistribution of a thymidine kinase-deleted mutant", Cancer Gene Therapy (Jan. 2000), 7(1):66-73.
Qin; et al., "Cancer gene therapy using tumor cells infected with recombinant vaccinia virus expressing GM-CSF", Human Gene Therapy (Oct. 1996), 7(15):1853-60.
Sanchez-Puig; et al., "Susceptibility of different leukocyte cell types to Vaccinia virus infection", Virol. J. (Nov. 2004), 1:10-17.

(Continued)

Primary Examiner — Kevin Kai Hill
(74) Attorney, Agent, or Firm — Pamela J. Sherwood; Bozicevic, Field & Francis LLP

(57) ABSTRACT

Compositions and methods are provided for the treatment of cancer. An immune effector cell population is pre-infected with an oncolytic virus. The combined therapeutic is safe and highly effective, producing an enhanced anti-tumor effect compared to either therapy alone. The methods of the invention thus provide for a synergistic effect based on the combined biotherapeutics.

29 Claims, 8 Drawing Sheets
(5 of 8 Drawing Sheet(s) Filed in Color)

(56) References Cited

OTHER PUBLICATIONS

Thorne; et al., "Future directions for the field of oncolytic virotherapy: a perspective on the use of vaccinia virus", Expert. Opin. Biol. Ther. (Aug. 2004), 4(8):1307-21.
Virus Life Cycle, web.archive.org/web/20030921205340/http://www.ucalgary.ca/~ceri/cmmb421prot/Virus+Life+Cycle.html, last visited Aug. 12, 2009.
Virus Replication, http://www.microbiologybytes.com/virology/3035Replication.html, last updated Oct. 22, 2004, last visited Aug. 12, 2009.
Edinger, Matthias, Revealing lymphoma growth and the efficacy of immune cell therapies using in vivo bioluminescence imaging, Blood, 101(2): 640-648, Jan. 15, 2003.
Byrd et al., "Primary Human Macrophages Serve as Vehicles for Vaccinia Virus Replication and Dissemination", Journal of Virology, Jun. 2014, pp. 6819-6831, vol. 88 No. 12, American Society for Microbiology, Washington, D.C.

* cited by examiner

IMMUNE EFFECTOR CELLS PRE-INFECTED WITH ONCOLYTIC VIRUS

This invention was made with Government support under contracts CA049605 and CA114747 awarded by the National Institutes of Health. The Government has certain rights in the invention.

BACKGROUND OF THE INVENTION

Neoplasia is a process that occurs in cancer, by which the normal controlling mechanisms that regulate cell growth and differentiation are impaired, resulting in progressive growth. This impairment of control mechanisms allows a tumor to enlarge and occupy spaces in vital areas of the body. If the tumor invades surrounding tissue and is transported to distant sites it will likely result in death of the individual.

The desired goal of cancer therapy is to kill cancer cells preferentially, without having a deleterious effect on normal cells. Several methods have been used in an attempt to reach this goal, including surgery, radiation therapy, and chemotherapy.

Local treatments, such as radiation therapy and surgery, offer a way of reducing the tumor mass in regions of the body that are accessible through surgical techniques or high doses of radiation therapy. However, more effective local therapies with fewer side effects are needed. Moreover, these treatments are not applicable to the destruction of widely disseminated or circulating tumor cells eventually found in most cancer patients. To combat the spread of tumor cells, systemic therapies are used.

The primary weapon against cancer is chemotherapy. However, chemotherapeutic agents are limited in their effectiveness for treating many cancer types, including many common solid tumors. This failure is in part due to the intrinsic or acquired drug resistance of many tumor cells. Another drawback to the use of chemotherapeutic agents is their severe side effects. These include bone marrow suppression, nausea, vomiting, hair loss, and ulcerations in the mouth.

Proposed alternative therapies include the administration of oncolytic viruses, and the use of viral vectors to deliver a transgene whose expression product activates a chemotherapeutic agent. The genetic engineering of viruses for use as oncolytic agents has initially focused on the use of replication-incompetent viruses. This strategy was hoped to prevent damage to non-tumor cells by the viruses. A major limitation of this approach is that these replication-incompetent viruses require a helper virus to be able to integrate and/or replicate in a host cell. These viruses are limited in their effectiveness, because each replication-defective retrovirus particle can enter only a single cell and cannot productively infect others thereafter. Therefore, they cannot spread far from the producer cell, and are unable to completely penetrate many tumors in vivo. More recently, genetic engineering of oncolytic viruses has focused on the generation of "replication-conditional" viruses in an attempt to avoid systemic infection, while allowing the virus to spread to other tumor cells. Replication-conditional viruses are designed to preferentially replicate in actively dividing cells, such as tumor cells. Thus, these viruses should target tumor cells for oncolysis, and replicate in these cells so that the virus can spread to other tumor cells.

However, while the virus-based approach has provided evidence of significant therapeutic effects in animal models of tumors, the method is limited by the efficiency of viral infection; the requirement of a helper virus or producer cell line for some viral vectors; tumor cell heterogeneity for the cellular factor(s) complementing viral mutant growth for other viral vectors; and antiviral immune responses.

A variety of immune cell-based cancer therapies have also been proposed, many of which rely on the identification of tumor-associated antigens that are often weak or expressed on only a subset of tumor cells. Cytokine induced killer (CIK) cells are a population of cells derived from human PBMC's following ex vivo expansion with γIFN, anti-CD3 antibody and IL-2. They bear phenotypic markers of NK and T cells, express NKG2D and have been found to mediate killing of tumor cells through recognition of a class of stress-associated ligands expressed on the tumor cell surface (NKG2D ligands). CIK cells therefore do not rely on specific antigens and they have also been shown to target a variety of tumors and exert their cytotoxic effects following systemic delivery. Previous pre-clinical imaging studies found that at 72 hours (h) after intravenous delivery signals from CIK cells were found primarily at the tumor site. However, tumor cell killing required effector to target ratios of five to ten CIK cells per tumor cell in vitro, and a dependence on over expression of NKG2D ligands on the tumor targets.

Targeted biological therapies hold tremendous potential for the treatment of cancers, yet their effective use has been limited by constraints on delivery and effective tumor targeting. There exists a need for a local therapy that provides for effective killing of tumor cells. The present invention addresses this need.

RELEVANT LITERATURE

Leemhuis et al. (2005) *Biol Blood Marrow Transplant* 11, 181-7 (2005); Lu & Negrin (1994) *J Immunol* 153, 1687-96; Kim et al. (2001) *Nat Med* 7, 781-7 (2001). Thorne & Kim (2004) *Expert Opin Biol Ther* 4, 1307-21. Puhlmann et al. (2000) *Cancer Gene Ther* 7, 66-73 (2000). Hamerman et al. (2005) *Curr Opin Immunol* 17, 29-35.

SUMMARY OF THE INVENTION

Methods are provided for the treatment of cancer, through administration to a patient of an effector cell population that is pre-infected with an oncolytic virus. The effector cells are preferably T cells, which may be autologous or allogeneic. In some embodiments, the cells are cytokine induced killer cells, which do not rely on recognition through the T cell antigen receptor for cytotoxicity. In other embodiments, the cells are tumor infiltrating T lymphocytes. The effector cells are infected with an oncolytic virus, preferably a replication competent virus, e.g. vaccinia, adenovirus, etc. Oncolytic viruses of interest are replication-selective or tropism modified viruses that are either only capable of entering into, or of completing a successful infection cycle within, transformed cells.

Pre-infection of effector cells with oncolytic virus resulted in a prolonged eclipse period where the virus remained within the cells until interaction with, and infiltration into, the tumor. The infected cells are preferably administered to the patient during the eclipse phase. In the combined therapeutic, the effector cells were shown to retain their ability to traffic to tumors. At the tumor site the oncolytic virus was released deep in the tumor rather than merely at the surface; thus the cell mediated delivery of the virus led to enhanced biodistribution within the tumor. In addition, the cytotoxic effects of the effector cells may be increased by viral replication in the tumor target. This combined therapeutic has been demonstrated to be safe, with minimal viral infection of normal tissues, and highly effective, producing an enhanced anti-tumor effect compared to either therapy alone. The methods of the invention thus provide for a synergistic effect based on the combined biotherapeutics.

Other objects and advantages of the present invention will become evident from the following detailed description of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other objects, features and many of the attendant advantages of the invention will be better understood upon a reading of the detailed description of the invention when considered in connection with the accompanying drawings which show as follows:

(FIG. 1A) Viral replication was followed for different vaccinia strains in CIK cells after infection at a multiplicity of infection (MOI) of 1.0 plaque forming units (PFU)/cell (* p=0.034, T12 test, SEM). (FIG. 1B) Viral replication of the same vaccinia strains in the B-cell lymphoma cell line OCI-ly8 (MOI of 1.0 PFU/cell). (FIG. 1C) Kinetics of replication of vvDD in CIK cells following infection at an MOI of 1.0 PFU/cell. Viral infectious units (PFU/ml) were titered separately in the cell and media fractions of the infected plate at times indicated. Cell-associated and cell-free viral titers are plotted to reveal viral replication kinetics. CIK cell numbers within infected or uninfected plates were counted at the same time points.

(FIG. 2A) UCI-101 target cells expressing luciferase were mixed with different numbers of CIK effector cells (ratios of 100:1, 50:1, 20:1 and 10:1 or target only). CIK effector cells had been pre-infected with vvDD for 24-h, 48-h or 72-h (MOI 1.0 PFU/cell). Luciferase output, as an indication of cytotoxicity, was measured using an IVIS50 system (Xenogen Corp.) after 4 h. (FIG. 2B) SKOV-3 target cells expressing luciferase, alone or pre-infected with vvDD (MOI 1.0 PFU/cell) for 24-h, were mixed with CIK cells at effector:target ratios of 20:1. Luciferase signal was measured after 4 h (p=0.0076, T-test, SEM). (FIG. 2C) UCI-101 or SKOV-3 cells alone or pre-infected with vvDD (MOI 1.0 PFU/ml for 8 h) were stained with anti-MICA/MICB antibody conjugated to PE and the numbers of cells expressing these cell surface markers were determined by FACS analysis. Isotype controls produced less than 1% positive staining.

(FIG. 3A) Mice received 1×10⁷ CIK cells pre-infected with vvDD-luc (MOI 1.0 PFU/cell) via tail vein injection (left) or 1×10⁷ PFU vvDD-luc via tail vein injection (right). Injections occurred on day 0. Animals were imaged at the times indicated (in days post therapy) using an IVIS200 system (Xenogen Corp.). Alternatively, vvDD-GFP was used (lower panel day 3) in an equivalent experiment, and animals were imaged using a Maestro (CRI, Boston Mass.) imaging system. (FIG. 3B) Quantification of light output per tumor is plotted relative to time 13 as an indication of viral replication and distribution. Values are averages for 3 animals per group, error bars are SEM; p=0.0079 at day 35 (T-test). (FIG. 3C) Tumors from animals receiving vvDD-GFP (1×10⁷ PFU) or 1×10⁷ CIK pre-infected with vvDD-GFP (MOI 1.0 PFU/cell) via tail vein injection. Sections (48 h post-injection) were stained with anti-CD31 (endothelial cell marker) (magnification 400×) (FIG. 3D) Tumor from animals receiving 1×10⁷ CIK cells conjugated to Cy5.5 (red) and pre-infected with vvDD-GFP (MOI 1.0 PFU/cell). Sections were stained with Sytox blue (DNA binding)(blue) and anti-GFP antibody (green) (tumors taken 72 h post-injection). Arrows indicate area of overlapping green and red, indicating infected CIK cells within the tumor (scale bar 100 $\mu$m).

(FIG. 4A) Kaplan-Meier survival curves of animals carrying UCI-101 or SKOV-3 intraperitoneal tumors (cell lines expressed luciferase and tumor burden was measured using bioluminescence imaging). Each animal received a single tail vein injection of either PBS; 1×10⁷ CIK cells; 1×10⁷ PFU vvDD; or 1×10⁷ CIK cells preinfected with vvDD (MOI 1.0 PFU/cell), n=8 animals/group. Combination therapy significantly increased survival compared to any other treatment (Logrank test; p=<0.05). (e.g. CIK+vvDD compared to vvDD alone; p=0.0072 (UCI-101) or 0.0379 (SKOV-3)). (FIG. 4B) The tumor burden (measured by bioluminescence imaging) for each individual animal was plotted against time. A single intravenous treatment was delivered on day 3 (arrows) of PBS (black) or combination therapy (green) (top) or CIK (red) or vvDD (blue) (bottom). Grey shaded area indicates range of tumor burden for the PBS treated group.

(FIG. 5A) Mice carrying subcutaneous SKOV-3 (top panel) or UCI-101 (bottom panel) tumors were treated (day 0) with a single intravenous injection of either 1×10⁷ CIK cells labeled with Cy5.5 (left animal) or 1×10⁷ Cy5.5 labeled CIK cells infected with vvDD-GFP (MOI 1.0) (right animal). Cy5.5 fluorescence was imaged using an IVIS200 system (Xenogen Corp.). A PBS control mouse was included 14 for comparison on day 2. (FIG. 5B) In an equivalent experiment, a mouse bearing an UCI-101 tumor was treated with 1×10⁷ CIK cells transfected with retrovirus to express luciferase and infected with vvDD-GFP (MOI 1.0) on day 0. Bioluminescence was imaged using an IVIS200. Arrows indicate locations of tumors.

(FIG. 6B) anti-GFP antibody: or (FIG. 6C) anti-MICA/B. Fluorescence was imaged, along with Cy5.5 fluorescence (FIG. 6D) using a Leica confocal microscope. An overlay image is also shown (FIG. 6E)

DETAILED DESCRIPTION OF THE EMBODIMENTS

Figures 1A, 1B, 1C:
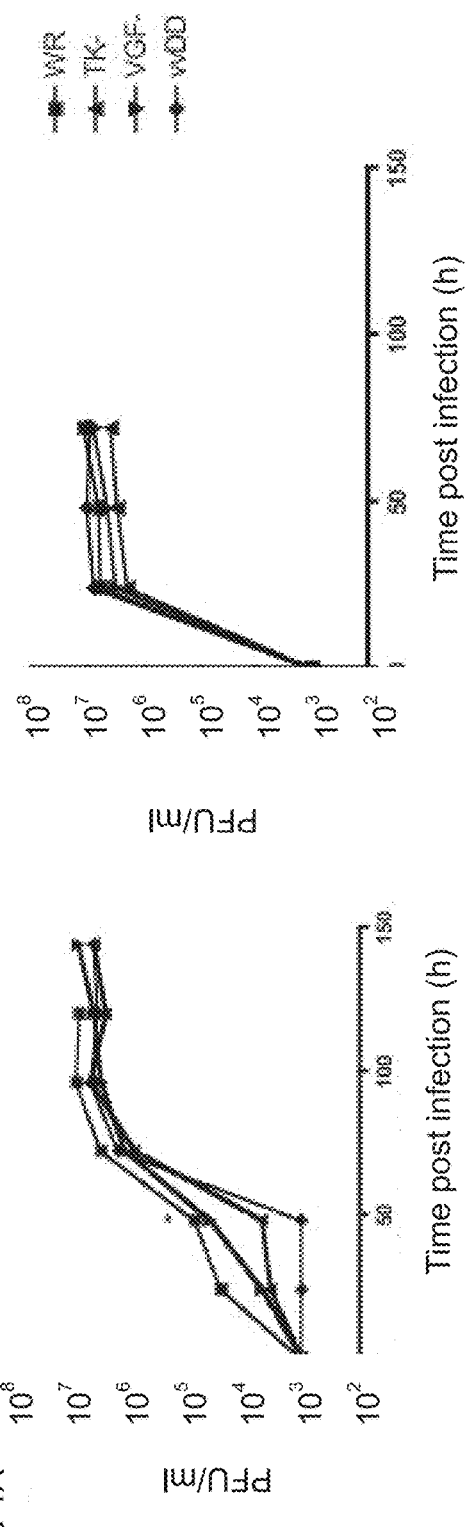
FIG. 1A-1C. Vaccinia virus displays unusual replication kinetics in CIK cells.

The objects and advantages of the present invention are achieved by a method of treating malignancy in a patient; comprising administering an effective amount of immune effector cells pre-infected with an oncolytic virus, to a patient afflicted with cancer. Oncolytic viruses of interest are replication-selective or tropism modified viruses that are either only capable of entering into, or of completing a successful infection cycle within, transformed cells.

It has been found that a surprising synergy is obtained by infecting immune effector cells with an oncolytic virus. The infection of the tumor cells sensitizes them to subsequent effector cell-mediated killing. Without limiting the scope of the invention, it is believed that the effect may be mediated by expression of proteins on the cell surface that are associated with cellular stress, and which enhance effector cell killing. Further, virus delivered via infected immune effector cells produced a more uniform biodistribution of infection within the tumor, even at locations distant to the tumor vasculature. The combination therapy was capable of producing dramatically increased survival compared to either therapy alone.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

As used herein, a "target cell" is a tumor cell in which the virus replicates. Usually a target cell is a mammalian cell, preferably a human cell.

A "host cell" includes an individual cell or cell culture which can be or has been a recipient of any virus and/or virus vector(s) of this invention. Host cells include progeny of a single host cell, and the progeny may not necessarily be completely identical (in morphology or of total DNA complement) to the original parent cell due to natural, accidental, or deliberate mutation and/or change. A host cell includes cells transfected or infected in vivo with a polynucleotide and/or a vector of this invention.

As used herein, the terms "neoplastic cells", "neoplasia", "transformed", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation. Neoplastic cells can be malignant or benign.

The term "gene" is well understood in the art and is a polynucleotide encoding a polypeptide. In addition to the polypeptide coding regions, a gene includes non-coding regions including, but not limited to, introns, transcribed but untranslated segments, and regulatory elements upstream and downstream of the coding segments.

"Replication" and "propagation" are used interchangeably and refer to the ability of a virus to reproduce or proliferate. This term is well understood in the art. For purposes of this invention, replication involves production of virus proteins and is generally directed to replication of the virus genome. Replication can be measured using assays standard in the art and described herein, such as a burst assay or plaque assay. "Replication" and "propagation" include any activity directly or indirectly involved in the process of virus manufacture, including, but not limited to, viral gene expression, production of viral proteins, nucleic acids or other components, packaging of viral components into complete viruses, and cell lysis.

The terms "polypeptide", "peptide" and "protein" are used interchangeably to refer to polymers of amino acids of any length. These terms also include proteins that are post-translationally modified through reactions that include glycosylation, acetylation and phosphorylation.

As used herein, "cytotoxicity" is a term well understood in the art and refers to a state in which one or more of a cell's usual biochemical or biological functions are perturbed. These activities include, but are not limited to, metabolism, cellular replication, DNA replication, transcription, translation, and uptake of molecules. "Cytotoxicity" includes cell death and/or cytolysis. Assays are known in the art which indicate cytotoxicity, such as dye exclusion, $^3$H-thymidine uptake, and plaque assays. The term "selective cytotoxicity", as used herein, refers to the cytotoxicity conferred by a virus on a target cell, compared to the cytotoxicity conferred by an virus on a non-permissive cell. Such cytotoxicity may be measured, for example, by plaque assays, reduction or stabilization in size of a tumor comprising target cells, or the reduction or stabilization of serum levels of a marker characteristic of the tumor cells or a tissue-specific marker, e.g., a cancer marker such as prostate specific antigen.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, rodents, primates, farm animals, sport animals, and pets.

An "effective amount" is an amount sufficient to effect beneficial or desired clinical results. An effective amount can be administered in one or more administrations. For purposes of this invention, an effective amount of the therapy is an amount that is sufficient to palliate, ameliorate, stabilize, reverse, slow or delay the progression of the disease state.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment. "Palliating" a disease means that the extent and/or undesirable clinical manifestations of a disease state are lessened and/or time course of the progression is slowed or lengthened, as compared to not administering vectors of the present invention.

Oncolytic Virus.

Oncolytic viruses are viruses, which, when brought into contact with tumor cells, are capable of killing those cells. Viruses of interest are replication-selective or tropism modified for tumor cells, and often have been genetically modified to reduce replication capability in non-transformed cells. Viruses of interest include adenovirus; herpes simplex virus-1; vaccinia virus; parvovirus; reovirus; Newcastle disease virus; and the like. Vaccinia virus is of particular interest.

As used herein, "virus" refers to the virus itself or derivatives thereof. The term covers all serotypes and subtypes and both naturally occurring and recombinant forms, except where otherwise indicated. An viral vector of the present invention can be in any of several forms, including, but not limited to, naked viral genomic DNA; a viral genome encapsulated in an virus coat; packaged in another viral or viral-like form (such as herpes simplex virus and AAV); encapsulated in a liposome; complexed with polylysine or other biocompatible polymer; complexed with synthetic polycationic molecules; conjugated with transferrin; complexed with compounds such as PEG to immunologically "mask" the molecule and/or increase half-life, or conjugated to a non-viral protein. For purposes of this invention, virus vectors are replication-competent in a target tumor cell.

Mechanistic approaches to tumor-selective replication include the use of viruses with inherent tumor selectivity (for example, Newcastle disease virus (NDV), reovirus, vesicular stomatitis virus (VSV) and autonomous parvovirus); deletion of entire genes (herpes simplex virus (HSV), adenovirus and vaccinia virus) or functional gene regions (adenovirus and poliovirus) that are necessary for efficient replication and/or toxicity in normal cells but are expendable in tumor cells; engineering of tumor/tissue-specific promoters into viruses to limit expression of gene(s) necessary for replication to cancer cells (adenovirus and HSV); and modification of the viral coat to selectively target uptake to tumor cells (adenovirus and poliovirus).

Specific modifications known in the art include modifications to the virus for tumor selectivity include deletion of viral genes necessary for replication in normal cells but not tumor cells, e.g. adenovirus E1B 55 kD deletion; HSV-1 ribonucleotide reductase subunit disruption; adenovirus E1A CR1 or CR2 deletion; poliovirus PV1 deletion; etc. Tumor specific promoter element may be used to drive expression of early viral genes, e.g. adenovirus E1A under the control of alpha fetoprotein promoter/enhancer; adenovirus E1A or E1B under the control of PSA promoter/enhancer; adenovirus E1A under the control of alpha fetoprotein promoter/enhancer; HSV-1 ICP4 gene under the control of albumin promoter/enhancer; etc. The virus may be engineered to express a tumor-selective receptor in the virus coat, e.g. adenovirus having a replacement of CAR/integrin-binding with a tumor targeting ligand; and the like.

The oncolytic virus may further comprise a coding sequence or coding sequences for a protein or proteins to be administered to the patient. In some embodiments, such proteins are those that are cytotoxic or cytostatic for tumor cells, e.g. tumor necrosis factor (TNF), interleukin-2 (IL-2), drugs that can be utilized in an effective chemotherapeutic regime, such as multiple drug resistant protein. The DNA encoding such active protein ingredient may be obtained from any convenient source and, depending on the protein chosen, can be synthesized chemically, recovered from a cDNA library, isolated from genomic DNA, or otherwise obtained by means known in the art.

Proteins of interest include any protein(s) which has a desired effect on an infected cell in the subject to be treated. Advantages of the drug delivery system of the invention are experienced especially when the protein operates within the cytoplasm of a target cell or is released from an infected or lysed cell to induce a cytotoxic or cytostatic effect on neighboring cells (bystander effect). For example, tumor necrosis factor (TNF) is capable of selectively killing tumor cells, but needs to transit the cell membrane to exert its effect. Other proteins, such as ribotoxins and the various colony-stimulating factors, also operate intracellularly.

It will be appreciated that viruses constructed to express two genes may include two proteins that have prophylactic or therapeutic value, or one gene could express a dominate selectable marker which would facilitate identifying cells transfected with the two gene construct. An example of a selectable marker would be resistance to G418 that is conferred on cells by the presence of the neomycin gene sequences. Alternatively a second gene may be used for imaging purposes, for example the Sodium Iodide symporter (NIS) gene or somatostatin receptor gene may be expressed in order to locate and quantify viral gene expression by delivery of a radiolabelled tracer followed by PET or SPECT imaging.

DNAs encoding the foregoing proteins are available in the art, and can be obtained bracketed with linker sequences for convenient manipulation, if desired. The nature of the delivery system is such that both genomic and cDNA sequences can be used, since introns can be processed in the environment transfected by the provirus. The protein drug can be encoded in the delivery virion to specify any form of the protein desired, for example, an active form, a mature form, a fused protein, a preprotein, or a preproprotein.

Vaccinia virus is of particular interest for the methods of the invention. Wild-type vaccinia virus is well tolerated following both intratumoral and intravesical treatment, and vaccinia viruses expressing tumor-associated antigens or proinflammatory cytokines have been well tolerated in a number of Phase I trials using subcutaneous, intradermal or intratumoral inoculation. Vaccinia, unlike most viruses proposed for use in virotherapy, has the advantage of some demonstrated systemic delivery potential. However, since the virus is capable of infecting many different cell types, only a small fraction of the inoculum of any strain used for virotherapy may reach the tumor. Therefore, development of an effective means of delivering viruses to tumor targets is necessary for the development of effective therapy.

In one embodiment of the invention, the oncolytic virus is a vaccinia virus. All vaccinia strains tested, including the wild-type strain, show unusual replication kinetics in immune effector cells, where there is an initial extended eclipse period of slow replication followed by a rapid burst of replication. The eclipse phase is at least about 1 day, usually at least about 2 days, and not more than about 4 days, usually after not more than about 3 days post-infection.

A number of vaccinia virus strains have been shown to display an eclipse phase in CIK cells, and may be used in the methods of the invention. The vaccinia strain Western Reserve (WR) alone or carrying deletions in the TK, VGF or both genes displayed an eclipse phase, which eclipse phase was 'enhanced' in the double deleted virus. Other vaccinia strains, including Wyeth and International Health Department (IHD) also displayed eclipse phases in CIK cells. In addition a variety of deletion mutations in the WR backbone also displayed an eclipse phase, of note deletions that enhanced the production of the EEV (Extracellular Enveloped Virus) form of the virus and deletions that prevented the production of extracellular IFN binding proteins.

Replication of vaccinia containing a deletion of the thymidine kinase (TK) gene has been shown to be restricted to cells with elevated cellular levels of thymidine kinase, e.g. dividing cells and tumor cells. Vaccinia with TK deletions will replicate both in the effector cell cultures, where cell division has been stimulated by anti-CD3 antibody, and in tumor cells. Thus, in one embodiment, the oncolytic virus is a vaccinia virus comprising a genetic modification that substantially eliminates active TK expressed from the viral genome.

Viral genes whose deletion does not effect, or enhances eclipse phase include, without limitation, TK, VGF, B5R (EEV producing); B8R (IFNγ binding protein); B18R (Type I IFN binding protein). The oncolytic virus may comprise a genetic modification that substantially eliminates active viral growth factor (VGF); B5R (EEV producing); B8R (IFNγ binding protein); or B18R (Type I IFN binding protein) expressed from the viral genome. For example, the VGF gene product promotes cellular growth after secretion from infected cells, by interacting with growth factor receptors. VGF deletions have been shown to restrict viral replication to cells with mutations in the Ras/MAPK/ERK pathway, offering additional tumor selectivity. In one embodiment, the oncolytic virus is a vaccinia virus comprising a genetic modification that substantially eliminates active TK expressed from the viral genome and active VGF expressed from the viral genome.

"Genetic alteration", or "mutation", to decrease expression of genes of interest as described above, refers to any alteration to a gene wherein the expression of that gene is significantly decreased, or wherein the gene product is rendered nonfunctional, or its ability to function is significantly decreased. The term "gene" encompasses both the regions coding the gene product as well as regulatory regions for that gene, such as a promoter or enhancer. Such alterations render the product of the gene non-functional or reduce the expression of the gene such that the viral mutant has the properties of the instant invention. Moreover, the invention encompasses mutants with one or more mutation(s) in one or more gene(s) of interest. Thus, by "a" is intended one or more. For example, "a mutation in a TK gene" means that there can be one or more mutations in one or more TK genes.

Ways to achieve such alterations include any method to disrupt the expression of the product of the gene or any method to render the expressed protein nonfunctional. Numerous methods known to disrupt the expression of a gene are known, including the alterations of the coding region of the gene, or its promoter sequence in the by insertions, deletions and/or base changes. (See, Roizman and Jenkins, Science 229: 1208 (1985)).

A preferred mutation is the deletion of nucleic acids from a gene. Methods for the construction of engineered viruses and for the genetic manipulation of DNA sequences are known in the art. Generally, these include Ausubel et al., Chapter 16 in Current Protocols in Molecular Biology (John Wiley and Sons, Inc.); Paoletti et al., U.S. Pat. No. 4,603,112 (July 1986). Virological considerations also are reviewed in Coen, in Virology, 1990 (2.sup.nd ed.) Raven Press, pages 123-150.

Immune Effector Cells.

Immune effector cells, for the purposes of the invention, are autologous or allogeneic immune cells having cytolytic activity against tumor cells. The effector cells may have cytolytic activity that does not require recognition through the T cell antigen receptor. Cells of particular interest include cells of the T and/or NK lineage, e.g. LAK cells, CIK cells, CTL, TIL cells, etc. The effector cells are typically obtained by culturing peripheral blood lymphocytes (PBL) in vitro with a cytokine and/or antigen combination that increases activation. In the methods of the invention, the activated effector cells are infected with virus, and administered to the patient. The cells are optionally separated from non-desired cells prior to culture, prior to administration, or both. Cell-mediated cytolysis of tumor cells by immunological effector cells is believed to be mediated by the local directed exocytosis of cytoplasmic granules that penetrate the cell membrane of the bound target cell.

Natural killer (NK) cells are cytotoxic cells belonging to a cell class responsible for cellular cytotoxicity without prior sensitization. IL-2-activated NK cells, the major effector population in lymphokine-activated killer (LAK) cells, are potent mediators of the lysis of autologous and allogeneic leukemic cells in vitro. LAK cells are non-B, non-T cells that are capable of recognizing cancer cells in a non-MHC-restricted fashion. LAK cells, which can be generated from either the normal or tumor-bearing host, appeared to represent a primitive immunosurveillance system capable of recognizing and destroying altered cells. NK cells often do not react with patient tumor cells unless they are activated by interferon, IL-2, or unless suppressor monocytes are removed from the effector cell population. IL-2 induces proliferation of T lymphocytes and NK cells and the production of IFN-gamma; it also results in the induction of LAK cells against previously NK-resistant cell preparations and cell lines. LAK activity can be generated from human and murine T cells following incubation with IL-2.

Most NK activity, as well as LAK activity, is mediated by the CD3⁻ large granular lymphocyte (LGL) cell population.

This lytic activity is observed against a variety of tumor cells and virally infected cells. Morphologically, NK cells are characterized as LGL cells containing a kidney-shaped nucleus and prominent azurophilic granules in their cytoplasm. Human LGL share both myelomonocytic (e.g., CD11) and T cell (e.g., CD2 and CD8)-related markers. However, the majority of human NK cell activity is mediated by CD3$^-$, CD56$^+$, and CD16$^+$ lymphocytes, although CD16$^-$ NK cells have also been characterized. The CD16c cells also have high levels of antibody-dependent cellular cytotoxicity (ADCC). The CD16$^-$ NK cells express markers similar to CD16$^+$ NK cells, including CD2, CD7, CD11b, CD38, CD45R, CD18, and p75 IL-2R. LAK cells have been utilized in vivo both in animals and in human beings for the treatment of melanoma, renal cell carcinoma, non-Hodgkin's lymphoma, and lung and colorectal cancers.

Cytotoxic T lymphocytes (CTL) reactive to autologous tumor cells are specific effector cells for adoptive immunotherapy. Induction and expansion of CTL is antigen-specific, and MHC restricted. Various types of cytokines other than IL-2 have also been reported to induce cytotoxic lymphocytes. A class of T lymphocytes with antitumor activity has been termed "tumor-infiltrating lymphocytes" (TIL). They possess more potent antitumor activity than LAK cells. They can be grown by culturing single-cell suspensions obtained from tumors in IL-2. Although lymphocytes comprise only a small subpopulation of the cells in a cancer nodule, some of these lymphocytes contain IL-2 receptors and grow under the influence of IL-2. Although tumor cells also grow in the culture, lymphocytes capable of eliminating the tumor cells have a selective growth advantage. After 2-3 weeks of culture, pure populations of lymphocytes without contaminating tumor cells are obtained. The major effectors of TIL cells are phenotypically CD3$^+$CD56$^-$CD8$^+$ and are MHC restricted. Cancer patients have been treated with ex vivo anti-CD3-activated killer cells and IL-2.

Cytokine-induced killer (CIK) cells are highly efficient cytotoxic effector cells obtained by culturing peripheral blood lymphocytes (PBLs) in the presence of IFN-gamma, IL-2 (or IL-12), and monoclonal antibody (MAb) against CD3, and optionally include IL-la. Cells may be cultured for at least about 1 week, at least about 2 week, at least about 3 weeks, or more, and usually not more than about 8 weeks in culture. The absolute number of CIK effector cells usually increases at least about 100-fold in such culture conditions, and may increase at least about 500-fold, at least about 1000-fold, or more.

CIK cells possess a higher level of cytotoxic activity and a higher proliferation rate than LAK cells. The phenotype of the cells with the greatest cytotoxicity expresses both the T-cell marker CD3 and the NK cell marker CD56. The expression of CD56 by the antigen is correlated with anti-tumor cytotoxicity. CD28, a major co-stimulatory signal of the TCR, is present on the cell surface only in a subset of CIK cells. CIK cells secrete IL-2, IL-6 and TNF-alpha. IL-4, IL-7, and IL-12 are not secreted. Most of these CD3$^+$CD33$^+$ cells co-expressed CD2, CD5, CD7, CD8 and HLA-DR but were negative for expression of CD4, CD13, CD14, CD15, and CD16. CD3cCD33c cells possessed no cytotoxic activity against tumor cells. CD3$^+$CD56$^+$ cells are expanded dramatically in CIK cell cultures. The percentage of CD3$^+$ CD56$^+$ cells reaches a plateau after approximately 1-2 months of culture. The dominant cell phenotype in CIK cell cultures expressed the alpha-, beta-T-cell receptor (TCR-$\alpha$/$\beta$). In comparison to NK cells, the cytotoxicity mediated by CD3$^+$CD56$^+$ cells is also non-MHC restricted in the absence of activation, but it is non-ADCC dependent, since these double-positive cells do not express CD16. Morphologically, these cells cannot be distinguished from NK cells.

A potent in vivo antitumor effect of CIK cells in an animal model can be achieved with as few as $1 \times 10^7$ cells. In humans, an effective dose is usually at least about $10^8$ cells, at least about $10^9$ cells, and may be $10^{10}$ cells, or more.

Immune effector cells useful in the methods of the invention have an "eclipse" period following infection with the oncolytic virus. It has been found that cells possessing this property include, without limitation, T cell lines and CIK cells, where vaccinia displayed a clear eclipse phase in these cells in culture.

Cancer, as used herein, refers to hyperproliferative conditions. The term usually denotes malignant cell populations. Such disorders have an excess cell proliferation of one or more subsets of cells, which often appear to differ from the surrounding tissue both morphologically and genotypically. The excess cell proliferation can be determined by reference to the general population and/or by reference to a particular patient, e.g. at an earlier point in the patient's life. Hyperproliferative cell disorders can occur in different types of animals and in humans, and produce different physical manifestations depending upon the affected cells.

Cancers include leukemias, lymphomas (Hodgkins and non-Hodgkins), sarcomas, melanomas, adenomas, carcinomas of solid tissue including breast cancer and pancreatic cancer, hypoxic tumors, squamous cell carcinomas of the mouth, throat, larynx, and lung, genitourinary cancers such as cervical and bladder cancer, hematopoietic cancers, head and neck cancers, and nervous system cancers, such as gliomas, astrocytomas, meningiomas, etc., benign lesions such as papillomas, and the like.

Cancers of interest include, but are not limited to, ovarian and breast cancer and lymphomas. Ovarian cancer is the second most commonly diagnosed gynecologic malignancy, the deadliest gynecologic malignancy, and the fourth leading cause of cancer-related deaths in women in the USA. About 1 in 70 women eventually develops ovarian cancer, and 1 in 100 women dies of it. Ovarian cancer affects predominantly perimenopausal and postmenopausal women.

Ovarian tumors are the most histologically diverse group of tumors. At least 80% of malignant ovarian tumors arise from the coelomic epithelium. The most common type is serous cystadenocarcinoma, which accounts for 75% of cases of epithelial ovarian cancer. Others include mucinous, endometroid, transitional cell, Brenner, clear cell, and unclassified carcinomas. The remaining 20% of malignant ovarian tumors are germ cell and sex cord-stromal cell tumors, which are nonepithelial in origin, and metastatic carcinomas to the ovary (most commonly, breast and GI carcinomas). Germ cell tumors, which arise from the primary germ cells of the ovary, occur in young women and are uncommon in women>30 yr. Malignant germ cell tumors include dysgerminomas, immature teratomas, endodermal sinus tumors, embryonal carcinomas, choriocarcinoma, and polyembryomas. Stromal malignancies include granulosa-theca cell tumors and Sertoli-Leydig cell tumors.

Ovarian cancer spreads by direct extension, by intraperitoneal implantation via exfoliation of cells into the peritoneal cavity, by lymphatic dissemination in the pelvis and para-aortic region, and, less commonly, hematogenously to the liver or lungs.

CA 125 is a cell surface glycoprotein detectable in 80% of cases of epithelial ovarian cancer. However, it is not specific to patients with ovarian cancer and, among premenopausal patients, can be mildly elevated in several benign disorders, including endometriosis, pelvic inflammatory disease, pregnancy, and leiomyomata uteri.

For patients with advanced-stage epithelial ovarian cancer, cytoreductive (tumor-debulking) surgery is advised to improve the efficacy of adjunctive therapies. The goal is to reduce the tumor burden so that the maximum diameter of the remaining implants is <1 cm. Cytoreductive surgery usually includes total hysterectomy, bilateral salpingo-oophorectomy, omentectomy, and excision of the tumor from any other sites. Rectosigmoid resection (usually with primary reanastomosis), radical peritoneal stripping, resection of diaphragmatic peritoneum, or splenectomy may be required. Prognosis for patients with advanced disease is directly related to the success of cytoreductive surgery.

Methods of Treatment

The methods of the invention involve the culture of immune effector cells in vitro, the infection of the immune effector cells with an oncolytic virus, and the administration of the infected cells to patient suffering from cancer. The treatment is intended to reduce or eliminate cancer in the patient. Also provided are compositions of immune effector cells infected with an oncolytic virus, which cells may be provided in a culture medium, in aliquots suitable for delivery to a patient, and the like.

The immune effector cells are usually generated from a fresh or frozen hematopoietic cell population. The source of cells may be autologous or allogeneic relative to the patient, but will usually be of the same species, e.g. human cells for human patients, mouse cells for a mouse recipient, etc. Cell populations include, but are not limited to, cell populations obtained from peripheral blood, spleen, lymph node, bone marrow, mobilized peripheral blood, umbilical cord blood, etc.

Procedures for separation can include, but are not limited to, physical separation, magnetic separation, using antibody-coated magnetic beads, affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation or any other convenient technique. The use of physical separation techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342). These procedures are well known to those of skill in this art.

The cells are cultured as described herein to provide for an activated cell population. Such culture typically reduces the number of non-desired cells, e.g. alloreactive T cells, etc. Undesired cells may also be removed by selection. Separation of the desired cells for engraftment will generally use affinity separation. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, LDS). Any technique may be employed which is not unduly detrimental to the viability of the selected cells.

The affinity reagents may be specific receptors or ligands for cell surface molecules, e.g. CD8, CD4, etc. In addition to antibody reagents, peptide-MHC antigen and T cell receptor pairs may be used; peptide ligands and receptor; ligand and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding agents are well-known to those skilled in the art.

The specific culture condition will be selected based on the type of effector cell that is desired. Where the effector cells are CIK cells, for example, the cells are washed and resuspended at in medium, e.g. RPMI, DME, etc. Interferon γ is added to culture at an effective concentration, e.g. at from about 100 to about 10,000 U/ml, usually around about 1000 U/ml. A ligand specific for CD3, e.g. monoclonal anti-CD3 antibody is added to the culture at an effective concentration, for example OKT3 may be used at a concentration of from about 1 to about 500 ng/ml. The medium is changed at IL-2 added at regular intervals. The effector cells are preferably taken when the CIK population has expanded.

The population of effector cells is infected with the cytolytic virus. Preferably the virus does not cause cytolysis of the effector cells in the period of time between infection and patient administration. As described herein, an eclipse period of from about 1 day to not more than about 4 days provides a window of time where the virus does not cause significant cytolysis of the effector cells.

If used as a packaged virus, the virus may be administered in an appropriate physiologically acceptable carrier. The multiplicity of infection will generally be in the range of about 0.001 to 100. The viruses may be administered one or more times.

Alternatively, viral DNA may be used to transfect the effector cells, employing liposomes, general transfection methods that are well known in the art (such as calcium phosphate precipitation and electroporation), etc. Due to the high efficiency of transfection of viruses, one can achieve a high level of modified cells.

The population of infected effector cells are injected into the recipient. Determination of suitability of administering cells of the invention will depend, inter alia, on assessable clinical parameters such as serological indications and histological examination of tissue biopsies. Generally, a pharmaceutical composition is administered.

Routes of administration include systemic injection, e.g. intravascular, subcutaneous, or intraperitoneal injection, intratumor injection, etc. Where the recipient animal is a human, the number of cells injected will usually be at least about $0.5 \times 10^8$ and not more than about $5 \times 10^{10}$, more usually at least about $1 \times 10^8$ or at least about $1 \times 10^9$.

The invention provides methods of suppressing tumor cell growth, comprising contacting a tumor cell with an infected effector cell of the invention such that the oncolytic virus enters the tumor cell, and there is selective cytotoxicity for the tumor cell. The composition may be administered once, or a series of times, e.g. daily, weekly, semi-monthly, etc. The efficacy may be monitored by standard methods as appropriate to the specific cancer, e.g. tumor size, biopsy, presence of tumor cells in the blood, etc. Tumor cell growth can be assessed by determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

"Suppressing" tumor growth indicates a growth state that is curtailed when compared to growth without contact with the cells of the invention.

The present invention also includes compositions, including pharmaceutical compositions, containing the infected effector cells described herein. Such compositions are useful for administration, for example, when measuring the effectiveness of cell killing in an individual. Preferably, these compositions further comprise a pharmaceutically acceptable excipient. These compositions, which can comprise an effective amount of an the infected effector cells of this invention in a pharmaceutically acceptable excipient, are suitable for systemic administration to individuals in unit dosage forms, sterile parenteral solutions or suspensions, sterile non-parenteral solutions or oral solutions or suspensions, oil in water or water in oil emulsions and the like. Formulations for parenteral and nonparenteral drug delivery are known in the art and are set forth in Remington's Pharmaceutical Sciences, 18.sup.th Edition, Mack Publishing (1990). Compositions also include lyophilized and/or reconstituted forms of the vectors of the invention.

The methods of the combination may be combined with conventional chemotherapeutic, radiologic and/or surgical methods of treatment. Cytotoxic agents that act to reduce cellular proliferation are known in the art and widely used. Such agents include alkylating agents, such as nitrogen mustards, e.g. mechlorethamine, cyclophosphamide, melphalan (L-sarcolysin), etc.; and nitrosoureas, e.g. carmustine (BCNU), lomustine (CCNU), semustine (methyl-CCNU), streptozocin, chlorozotocin, etc. Antimetabolite agents include pyrimidines, e.g. cytarabine (CYTOSAR-U), cytosine arabinoside, fluorouracil (5-FU), floxuridine (FUdR), etc.; purines, e.g. thioguanine (6-thioguanine), mercaptopurine (6-MP), pentostatin, fluorouracil (5-FU) etc.; and folic acid analogs, e.g. methotrexate, 10-propargyl-5,8-dideazafolate (PDDF, CB3717), 5,8-dideazatetrahydrofolic acid (DDATHF), leucovorin, etc. Other natural products include azathioprine; brequinar; alkaloids and synthetic or semisynthetic derivatives thereof, e.g. vincristine, vinblastine, vinorelbine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithromycin); anthracenediones, e.g. mitoxantrone; azirinopyrrolo indolediones, e.g. mitomycin; and the like. Other chemotherapeutic agents include metal complexes, e.g. cisplatin (cis-DDP), carboplatin, etc.; ureas, e.g. hydroxyurea; and hydrazines, e.g. N-methylhydrazine. Other anti-proliferative agents of interest include immunosuppressants, e.g. mycophenolic acid, thalidomide, desoxyspergualin, azasporine, leflunomide, mizoribine, azaspirane (SKF 105685), etc. The antineoplastic agents taxols (or taxanes) hyperstabilize polymerized microtubules, leading to mitotic arrest and cytotoxicity in proliferating cells. Taxanes (or taxols), such as paclitaxel, docetaxel, etc. are of interest. Also of interest are the microtubule stabilizing epothilones (see Bollag et al. (1995) Cancer Research, Vol 55, Issue 11 2325-2333, herein incorporated by reference with respect to teachings of the class, and use thereof of these chemotherapeutic agents), e.g. epothilone A and epothilone B. Retinoids, e.g. vitamin A, 13-cis-retinoic acid, trans-retinoic acid, isotretinoin, etc.; carotenoids, e.g. beta-carotene, vitamin D, etc. Retinoids regulate epithelial cell differentiation and proliferation, and are used in both treatment and prophylaxis of epithelial hyperproliferative disorders.

The present invention relates to the selective killing of neoplastic cells by combined viral mediated oncolysis and immune effector therapy, which combination provides a synergistic benefit when compared to either of the single therapies. The invention provides for oncolytic virus infected immune effector cells, a method of killing neoplastic cells using oncolytic virus infected immune effector cells, and a pharmaceutical composition containing oncolytic virus infected immune effector cells. In the combined therapeutic, the effector cells were shown to retain their ability to traffic to tumors. At the tumor site the oncolytic virus was released deep in the tumor rather than merely at the surface; thus the cell mediated delivery of the virus led to enhanced biodistribution within the tumor. In addition, the cytotoxic effects of the effector cells may be increased by viral replication in the tumor target. This combined therapeutic has been demonstrated to be safe, with minimal viral infection of normal tissues, and highly effective.

It has been shown that the effector cells of the invention can be used to deliver oncolytic virus to a recipient capable of mounting an anamnestic response against the oncolytic virus, e.g. a vaccinia virus can be successfully delivered to a patient previously immunized with vaccinia. This property overcomes a limitation of previously described viral therapy, where a single agent, e.g. an oncolytic virus, is ineffective in repeat doses or in vaccinated individuals due to the recipient immune response. It has been found that a polyclonal, anti-vaccinia antibody failed to recognize CIK cells infected with vaccinia, although the antibody did recognize tumor cells infected with vaccinia. VIG (vaccinia immunoglobulin) is an FDA approved treatment for adverse events following smallpox vaccination. Doses of VIG that completely neutralized vaccinia (prevented vaccinia from infecting a cell layer following 2 h of exposure to VIG) had no effect on the ability of infected CIK cells to transfer virus to a cell layer. Animals treated with vaccinia (or infected CIK cells) produced CTLs (cytotoxic T lymphocytes) that could recognize infected tumor cells, but not infected CIK cells. Tumor bearing and immunized mice were treated (IV) with vaccinia or infected CIK cells. There was very little evidence of vaccinia in the tumor when it was delivered alone. There were multiple areas of positively stained cells (for vaccinia infection) within the tumors when infected CIK cells were used. Tumor bearing animals treated with high doses (10× therapeutic levels) of VIG, and then treated with infected CIK cells still produced signal (bioluminescence imaging from virally encoded luciferase) from within the tumor.

EXPERIMENTAL

Example 1

Targeted biological therapies hold tremendous potential for the treatment of cancers, yet their effective use has been limited by constraints on delivery and effective tumor targeting. Here we combine an immune effector cell population; cytokine induced killer (CIK) cells, with a complementary oncolytic viral therapy as an effective treatment of ovarian cancer. CIK cells, an ex vivo expanded population of cells derived from human peripheral blood, were used to deliver a replication competent vaccinia virus carrying genetic deletions that restrict its replication to malignant cells. Pre-infection of CIK cells with oncolytic vaccinia virus resulted in a prolonged eclipse period where the virus remained within the CIK cells until interaction with, and infiltration into, the tumor. In this combined therapeutic not only did the CIK cells retain their ability to traffic to ovarian tumors, but once at the tumor site the oncolytic virus was released deep in the tumor rather than merely at the surface; cell mediated delivery of the virus led to enhanced biodistribution within the tumor. In addition, the cytotoxic effects of the CIK cells were increased by viral replication in the tumor target. This combined therapeutic was both safe, with minimal viral infection of normal tissues, and highly effective, producing a dramatically enhanced anti-tumor effect compared to either therapy alone. This effective new biological approach for the treatment of cancer, demonstrates that synergistic effects of combined biotherapeutics can be used to effectively kill difficult-to-treat cancers.

Viral replication kinetics were determined with selected vaccinia strains in CIK cells and compared to the parental strain (Western Reserve, WR). All vaccinia strains (including WR) displayed unusual replication kinetics in CIK cells (FIG. 1a) compared to the very rapid and lytic replication seen in other cell lines such as the lymphoma OCI-ly8 (FIG. 1b). There appeared to be a two-step growth curve in the CIK cells, with an initial extended eclipse period of slow replication followed by a rapid burst of replication between 48 and 72 h post-infection. Replication of vaccinia containing a deletion of the thymidine kinase (TK) gene has been shown to be restricted to cells with elevated cellular levels of thymidine kinase as observed in the G2- and S-phase of the cell cycle of normal cells. In cancer cells TK activity is constitutively high, and therefore vaccinia with TK deletions should replicate both in the CIK cultures, where cell division has been stimulated by anti-CD3 antibody, and in tumor cells. We observed replication of the TK vaccinia mutants in CIK cells (FIG. 1a), however, the amount of infectious virus produced during the eclipse phase was reduced relative to WR, and this served to accentuate the two-step replication kinetics.

The viral growth factor (VGF) gene product promotes cellular growth after secretion from infected cells, by interacting with growth factor receptors. VGF deletions have been shown to restrict viral replication to cells with mutations in the Ras/MAPK/ERK pathway offering additional tumor selectivity. Deletion of VGF was found to have a minimal effect on viral replication in CIK cells (FIG. 1a), and infection of CIK cells with a double deleted vaccinia virus (vvDD), containing deletions in both TK and VGF produced almost no virus during the first 48 h (FIG. 1c). After this time, virus appeared to begin to accumulate within infected CIK cells, before being released as the cells lyse. A high degree of tumor selectivity has previously been demonstrated for the double deleted virus, both in vitro and in a variety of models in vivo. For these reasons vvDD is used throughout the remainder of this study.

Figure 2A:
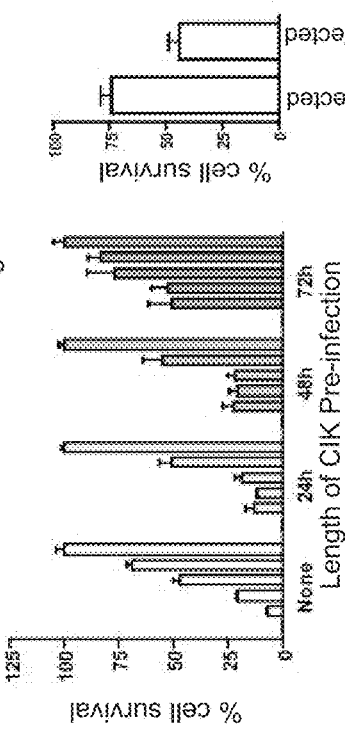
FIG. 2A-2C. CIK cells retain their ability to kill target cells despite pre-infection with vvDD, and infection of CIK-resistant target cells with vvDD increases their susceptibility to CIK-mediated killing due to NKG2D ligand expression.
Figure 2B:
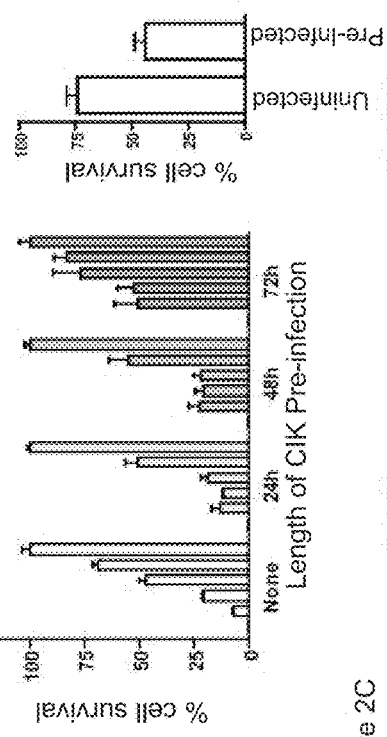
Figure 2C:
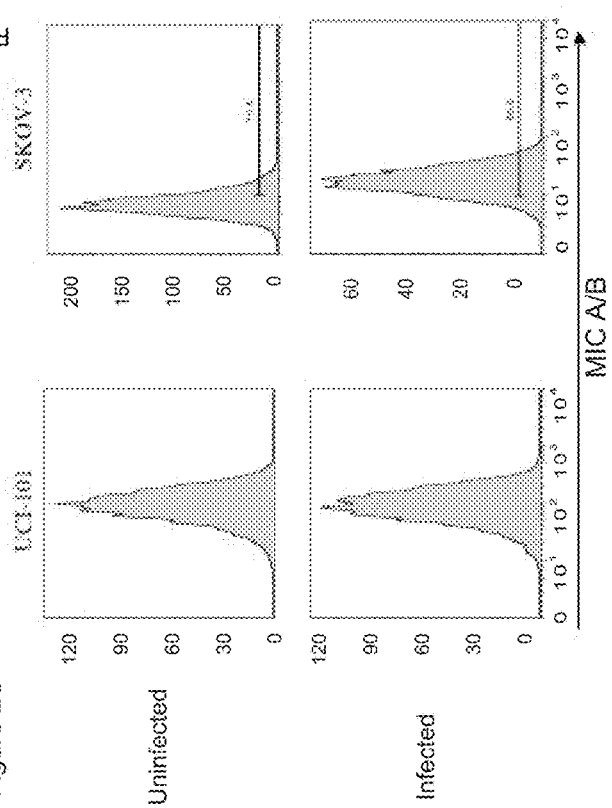

Further cell culture experiments were performed to examine the relationship between CIK cells and vvDD. A bioluminescence based cell survival assay was used to assess whether infected CIK cells can retain the ability to recognize and destroy target ovarian tumor cell lines (FIG. 2a). It was found that even after extended periods of infection (of at least 48 h), CIK cells remained functionally active and were able to destroy tumor targets including human ovarian cancer cell lines. In addition, it was found that infection of a CIK-resistant ovarian tumor cell (SKOV-3) with vvDD sensitized them to subsequent CIK-mediated killing (FIG. 2b, p=0.0076). CIK cells recognize NKG2D ligands on target cells, which are usually up-regulated under conditions of cellular stress, such as are encountered within a tumor environment or following viral infection. Two of the best characterized NKG2D ligands in humans are MICA and MICB, and it was found that levels of these proteins expressed on the surface of ovarian tumor cells corresponded to their sensitivity to CIK cell-mediated killing (FIG. 2c). MICA or MICB was expressed on the surface of the sensitive UCI-101 cell line, but not the resistant SKOV-3 cell line. However, infection of the SKOV-3 cell line with vvDD resulted in an increase in the percentage of cells expressing MICA or MICB, providing an explanation for the increased sensitivity of this resistant tumor to CIK-mediated killing (FIG. 2b).

Figures 5A, 5B:
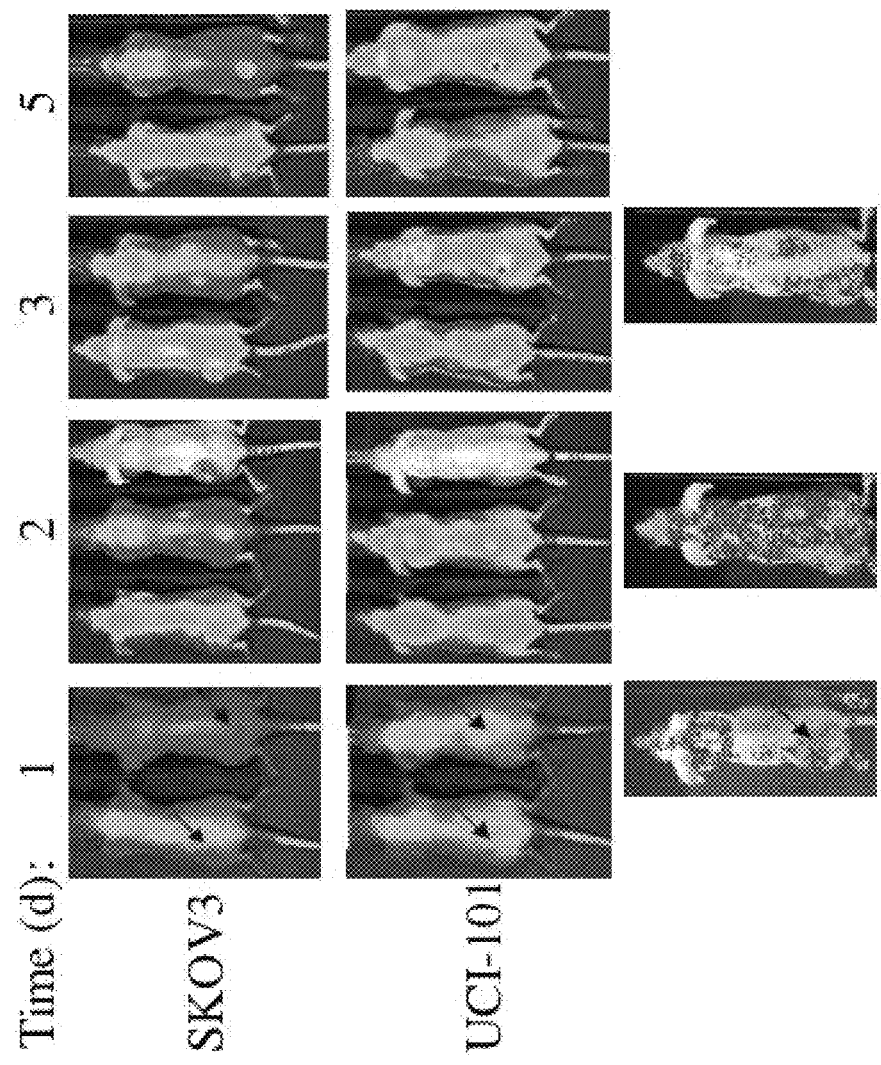
FIG. 5A-5B. Fluorescence and bioluminescence imaging of trafficking of uninfected and vvDD infected CIK cells.
Figures 6A, 6B, 6C, 6D, 6E:
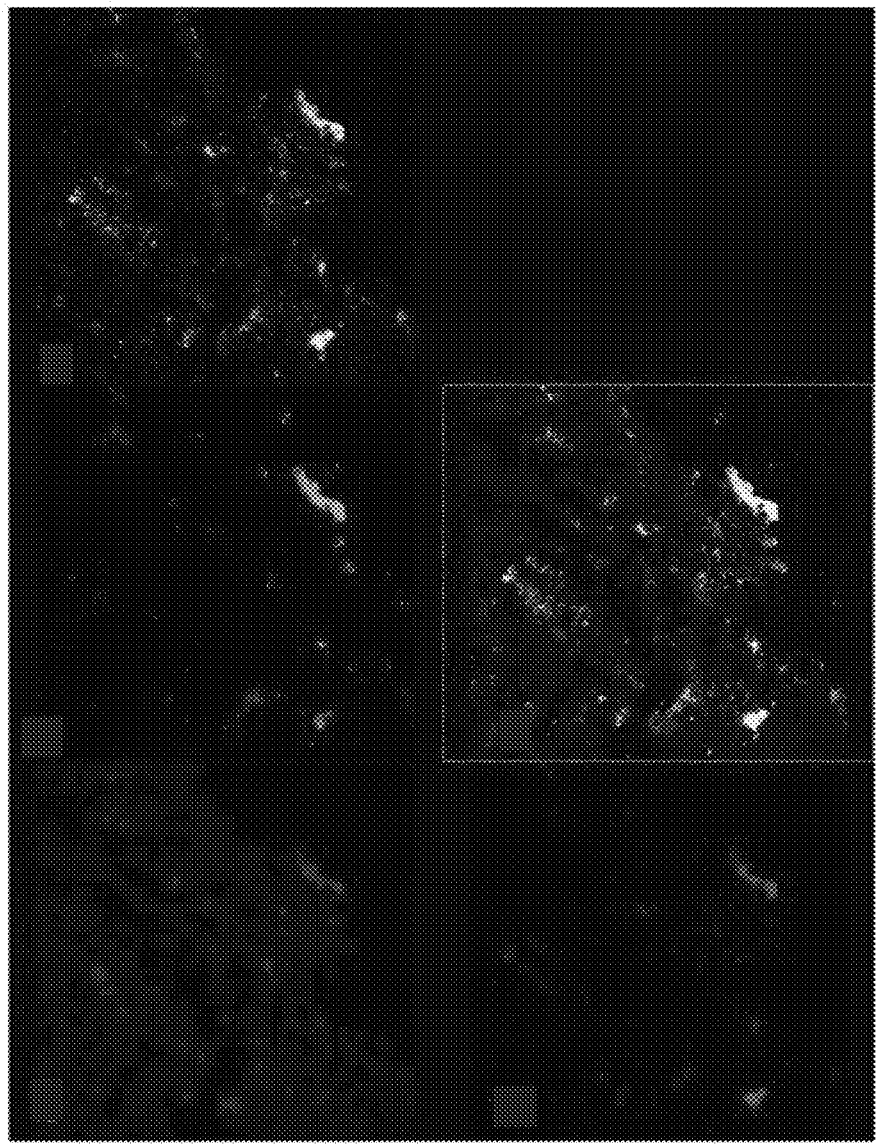
FIG. 6A-6E. Immunofluorescence microscopy of MICA/B expression in a treated SKOV-3 tumor. A mouse bearing a subcutaneous SKOV-3 tumor was treated with a tail vein injection of 1×10⁷ CIK cells labeled with Cy5.5 and infected with vvDD-GFP (MOI 1.0). Tumors were recovered 48 hours after treatment and frozen sections were stained with (FIG. 6A) a nuclear dye (Sytox Blue, Molecular Probes)

In vivo non-invasive imaging experiments were then performed in order to assess both the ability of pre-infected CIK cells to traffic to ovarian tumors and the subsequent biodistribution of virus compared to that following intravenous injection of virus alone. Conjugation of a fluorescent dye (Cy5.5) to the CIK cells prior to intravenous delivery enabled visualization of dye-labeled cells at the tumor site. Preinfection with vvDD did not affect the trafficking of CIK cells to UCI-101 tumors (Supplementary FIG. S1a), this was verified with CIK cells labeled through expression of luciferase (FIG. 5b). Since viral infection was shown to increase NKG2D ligand expression and sensitize SKOV-3 cells to CIK cytotoxicity in culture, we tested the effect of preinfected CIK cells on this otherwise resistant target cell. Cy5.5-labeled CIK cells, with or without pre-infection with vvDD, were intravenously delivered to mice bearing SKOV-3 tumors. CIK cells alone did not reduce the tumor burden, presumably due to lack of recognition, and no accumulation of CIK cells was observed at the tumor site (FIG. 5a). However, vvDD delivered along with the pre-infected CIK cells led to infection of the tumors and subsequent MICA or MICB up-regulation and CIK accumulation (followed by release of further vvDD within the tumor). This was verified by immunofluorescence microscopy, with the sites of CIK infiltration within the SKOV-3 tumor corresponding to areas of vvDD gene expression and MICA or MICB up-regulation (FIG. 6).

Figure 3A:
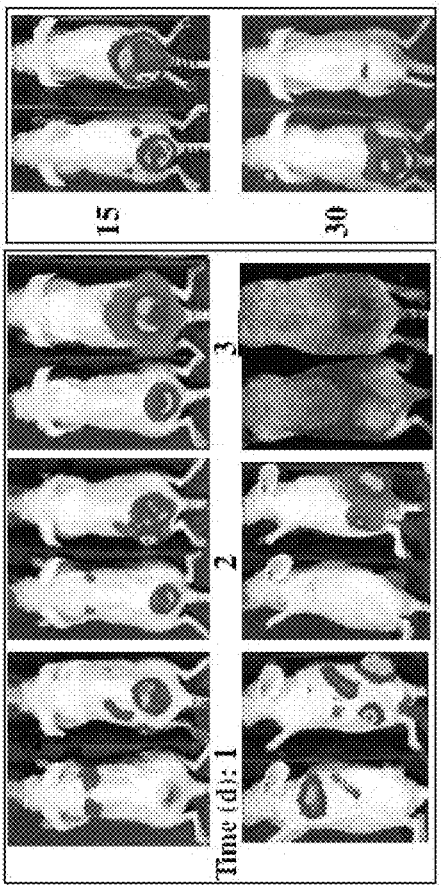
FIG. 3A-3D. Biodistribution of vvDD expressing luciferase delivered to mice bearing subcutaneous UCI-101 tumors either alone or within CIK cells and immunofluorescence microscopy of tumor sections (UCI-101).
Figure 3D:
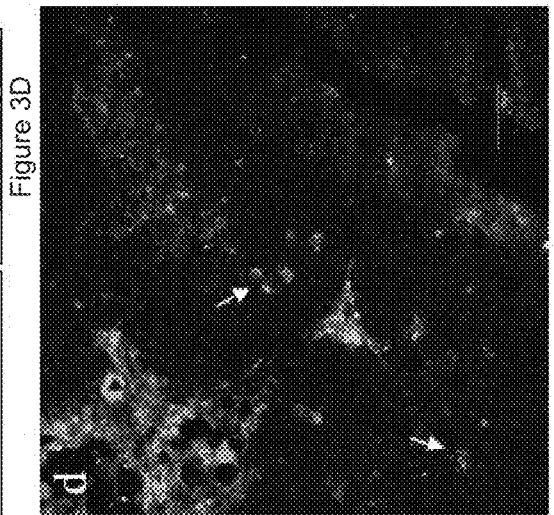
Figure 3B:
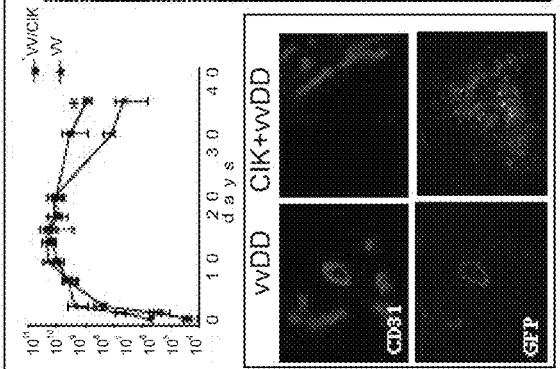

Using luciferase labeled vvDD and in vivo bioluminescence imaging, it was possible to follow the biodistribution and duration of viral gene expression for virus delivered alone or within CIK cells (FIG. 3a). Initial infection patterns at 24 h post injection showed viral gene expression within the lung, liver and spleen regardless of delivery method. However the ratios were different, with virus delivered alone leading to signals predominantly from the spleen, and virus delivered via CIK cells leading to signal predominantly from the lungs. The systemic delivery potential of vaccinia and the vvDD virus has been described previously. We observed tumor signal within 24 h following intravenous delivery of virus alone, whereas the virus within CIK cells did not lead to detectable signal at the tumor site until 48 h post delivery (which is similar to the time frame required for delivery of CIK cells to tumors), by this time very little signal was detected in any organs other than the tumor. Equivalent levels of signal, indicative of viral gene expression, were reached using both delivery methods by 5 days post treatment (FIG. 3b). Furthermore, signal from CIK cell-delivered virus was sustained within the tumor for longer periods of time compared to virus alone (p=0.0079 at day 35). It was observed that the bioluminescent signal within the tumor when virus was delivered alone appeared more sporadic relative to the more uniform signal produced from tumors treated with the combined therapy. This was also seen in an equivalent experiment using fluorescence imaging and a GFP expressing strain of vvDD (FIG. 3a).

Figure 3C:
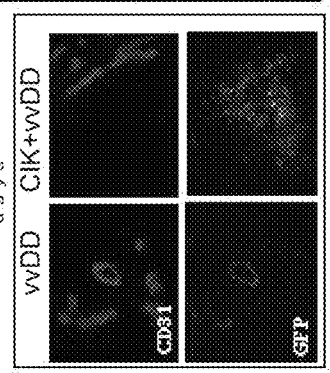
Figure 7:
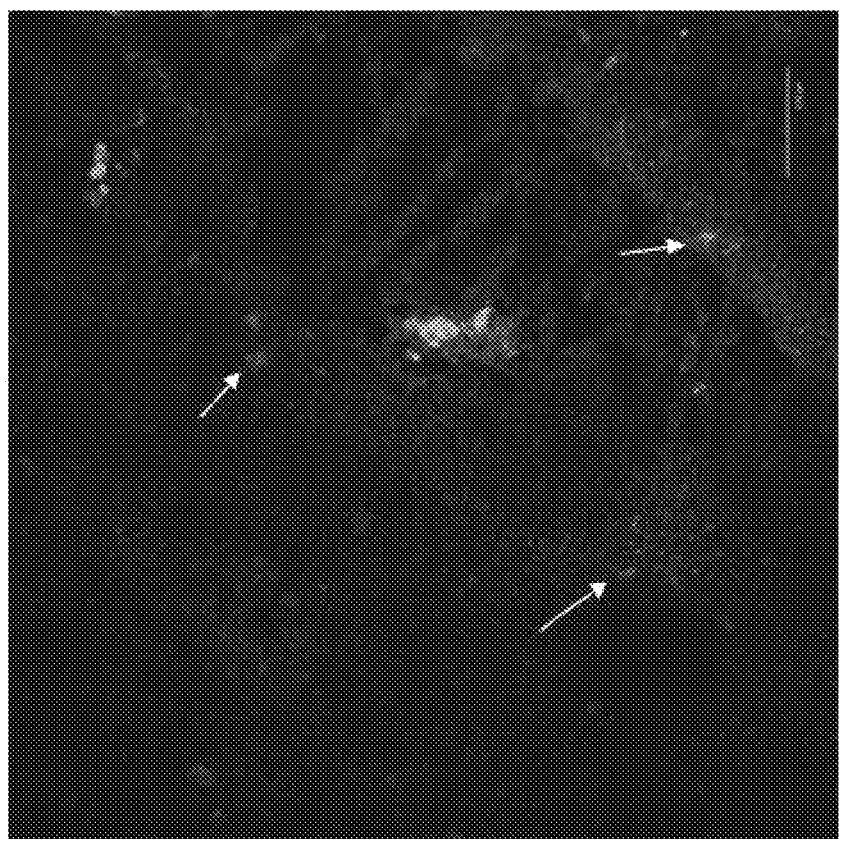
FIG. 7. Immunofluorescence microscopy of CIK delivery of vvDD in a UCI-101 tumor. A mouse bearing a subcutaneous UCI-101 tumor was treated with a tail vein injection of 1×10⁷ CIK cells labeled with Cy5.5 and infected with vvDD-GFP (MOI 1.0). Tumors were recovered 24 hours after treatment and frozen sections were stained with a nuclear dye (Sytox Blue, Molecular Probes) and anti-GFP antibody (green). Fluorescence was imaged, along with Cy5.5 fluorescence (red) using a Leica confocal microscope. An overlay image is shown. >Style tag for figure legends.

A more uniform distribution of viral infection following CIK-mediated delivery suggests penetration into the tumor, which along with sustained viral gene expression, would lead to increased tumor destruction. Although vaccinia virus vectors alone can both reach the tumor and spread very efficiently from cell to cell, we observed that their initial infection was limited to cells surrounding the tumor vasculature (FIG. 3c), and so they do not easily spread to more distant regions of the tumor. CIK cells however, once within the tumor environment are capable of actively extravascating from the vasculature, and it was predicted that preinfected CIK cells would carry oncolytic viruses into the tumor mass. We observed that virus delivered via infected CIK cells produced a more uniform biodistribution of infection within the tumor, even at locations distant to the tumor vasculature (FIG. 3c). Further immunofluorescence microscopy was used to show that at 24 h post delivery infected CIK cells could be found within the tumor (FIG. 7), demonstrating that they can deliver the viral agent to the tumor. By 72 h post treatment, initial sites of tumor cell infection can be seen at the edge of the tumor and surrounding the vasculature, however, infected CIK cells can be seen at locations distant to these sites of preliminary infection (FIG. 3d, arrows).

Figures 4A, 4B:
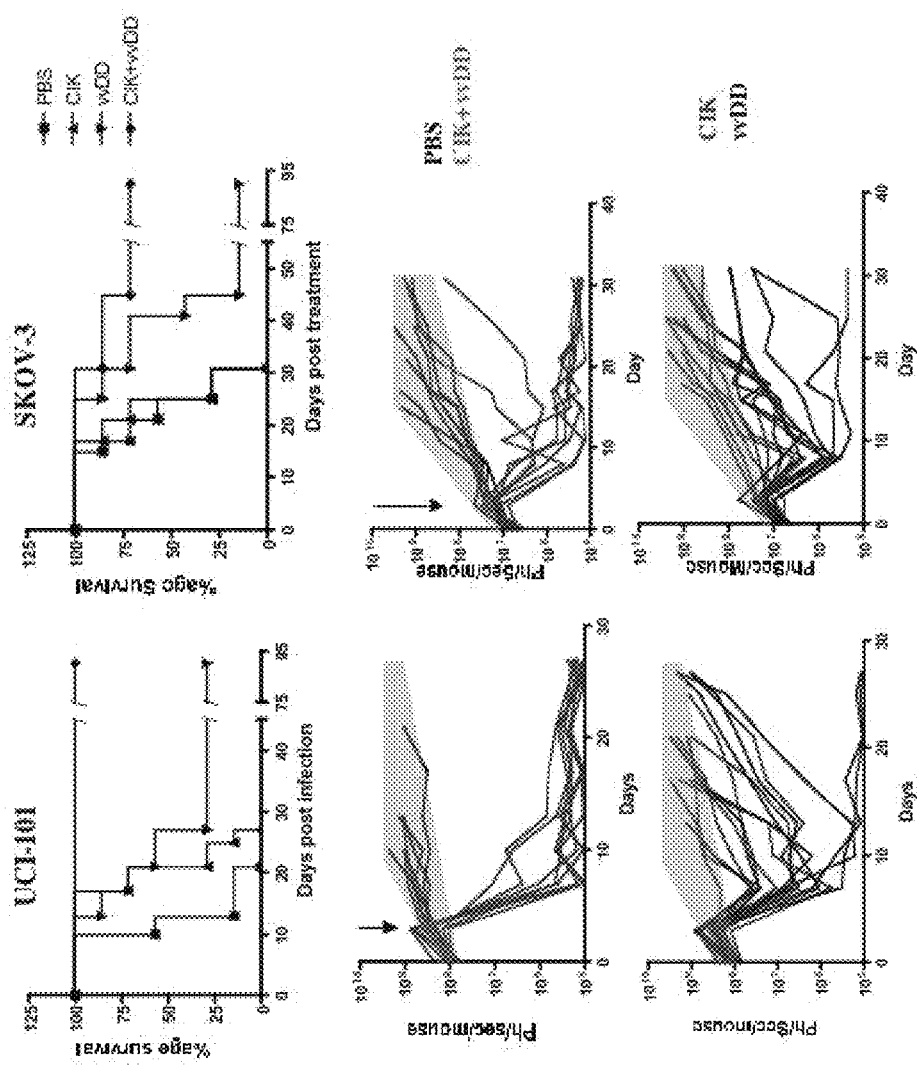
FIG. 4A-4B. Survival and tumor burden of animals bearing UCI-101 or SKOV-3 tumors.

Lastly to demonstrate synergistic efficacy the survival of animals bearing intraperitoneal ovarian tumors was followed after treatment via the tail vein with a single dose of either agent alone or with the combination biotherapy (FIG. 4a). CIK cells alone were able to marginally extend survival in the mice with sensitive UCI-101 tumors but had no effect in mice with the resistant SKOV-3 tumor. vvDD was also able to marginally increase survival in both these models, with some animals showing complete responses (FIG. 4a). However, the combination therapy was capable of producing dramatically increased survival (p=<0.01) compared to either therapy alone, with 100% complete responses among the animals bearing UCI-101 tumors. The combination therapy also displayed increased efficacy against SKOV-3 tumors compared to just the vvDD vector (p=0.0379), despite the fact that the CIK cells alone had no effect against these tumors. Plots of the tumor burden in individual animals (FIG. 4b) indicated that single vvDD or CIK cell therapy against sensitive tumors produced an initial response but incomplete eradication of the tumor leading to subsequent relapse. Complete responses were followed for up to 90 days without relapse.

Here we combine two biological therapies in such a way that we are able to harness the benefits of both and produce a new combination therapy that far exceeds the effectiveness of either alone. CIK cells were used to systemically deliver the oncolytic vaccinia virus, vvDD, efficiently and specifically to the site of the tumor. The oncolytic virus can then act to increase the tumor cell killing potential of the CIK cells. In addition to this however, we have found that the virus does not affect CIK cell function, but can sensitize tumor cells to CIK cell-mediated killing. Finally the CIK cells can transport the virus deep within the tumor, producing a more uniform biodistribution of viral infection of tumor cells within the cancer. The resulting targeted, biological therapy therefore displays systemic delivery potential, minimal toxicities and has significant anti-tumor effects.

Methods.

Cells and Viruses.

Human ovarian cancer cell lines were SKOV3 (obtained from ATCC) and UCI-101. Stably transduced versions of both cell lines were produced by retroviral infection in order to produce cells expressing click beetle red luciferase and puromycin (for selection). Growth characteristics of the transfected cells were compared to the parental strains in vitro to verify no effects due to the retroviral insertion. The human B cell lymphoma cell line (OCI-ly8) has been previously characterized. The expansion of CIK cells has been described previously by Lu & Negrin (1994) *J Immunol* 153, 1687-96. The strains of vaccinia were wild type Western Reserve (obtained from ATCC), Western Reserve containing a single deletion in the viral thymidine kinase (TK) gene, and expressing luciferase containing a single deletion in the VGF gene and expressing beta-galactosidase and the double deleted virus (vvDD) containing deletions in both the thymidine kinase and VGF genes and expressing GFP from within the site of the TK gene or expressing luciferase from the TK gene (constructed by homologous recombination of the VGF deleted virus and the plasmid pSC-65 containing the firefly luciferase gene from pGL3 (Promega)).

Viral Replication and Plaque Assays.

Cell lines to be assayed were infected by addition of virus at the multiplicity of infection (MOI) (Plaque Forming Units (PFU)/cell) indicated. After 2 h of infection, media was changed and at various times either media alone was retained or cells retained in PBS, or else media and cells were collected together. Cells were lysed by three cycles of freeze/thaw in order to release intracellular virus. Plaque assay was performed in 6-well plates on the BS-C-1 cell line (obtained from ATCC).

Cellular Cytotoxicity Assay.

Tumor cell lysis by effector cells was quantified by measuring the luciferase activity of surviving target cells. Target cells expressing luciferase were plated into black-walled 96-well plates at $1 \times 10^4$ cells/well. Effector cells were then added at specified effector to target ratios; all ratios (as well as target only wells) were plated in triplicate and incubated for 4 h at 37° C., 5% $CO_2$. Luciferin was then added to each well (2 µl of 30 mg/ml luciferin (Xenogen Corp)) and light output (photons·second$^{-1}$/well) measured on an IVIS 50 imaging system (Xenogen Corp). Percent cytotoxicity was then determined relative to control wells (target only or target only pre-treated with 70% ethanol).

FACS Assays.

FACS assays were performed on samples of cells alone or cells preinfected with vvDD expressing GFP. Cells were then stained with anti-MICA/B antibody conjugated to PE (BD Pharmingen) at a dilution of 1:200. Samples and controls were run on a FACScaliber (Becton Dickinson).

Mouse Tumor Models.

All mouse studies used CD1 nu/nu female mice aged 8 to 10 weeks (obtained from Charles River). All animal studies were performed according to Stanford IACUC approval. Tumors were formed in these animals by injection of $1 \times 10^6$ tumor cells either subcutaneous or intraperitoneally. Animals injected subcutaneously were treated by a single tail vein injection once palpable tumors of 50-100 mm$^3$ were formed (tumor size was followed by caliper measurement or bioluminescence imaging as indicated). Animals injected intraperitoneally received luciferase labeled tumor cells only and were imaged regularly by bioluminescence imaging and treated with a single intravenous tail vein injection of therapeutic as described 3 days after injection of labeled tumor cells. Bioluminescence imaging was used to confirm tumor cell light output was increasing prior to treatment. Non-invasive imaging assays. Both bioluminescence and fluorescence imaging modalities were incorporated in order to image tumor cells, virus or CIK cell biodistribution. Animals were anesthetized and injected with luciferin (150 mg/kg) 5 minutes prior to bioluminescence imaging. Animals were placed on a warmed stage (37° C.) and imaged using an IVIS 200 system (Xenogen Corp) for bioluminescence or Cy5.5 in vivo fluorescence imaging and a Maestro (CRI) for GFP imaging. Whenever fluorescent imaging was used, an initial background image was first taken for background subtraction immediately before the fluorescent image, and no luciferin was injected. Appropriate filter sets were used for Cy5.5 and GFP imaging.

Labeling of CIK Cells for Imaging.

CIK cells were either labeled with click beetle red luciferase by retroviral transduction, or with Cy5.5 NHS ester (Amersham Biosciences, GE).

Immunofluorescence Microscopy.

Tumors from animal treated with Cy5.5 labeled CIK cells and/or vvDD-GFP were frozen in OCT and sectioned (8-10 microns). Tissue slices were fixed in acetone, blocked with 2% FCS and stained using primary antibodies to CD-31 or GFP (Molecular Probes) as indicated. Secondary staining was with AlexaFluor conjugated antibodies (Molecular Probes) and nuclear staining with Sytox Blue (Molecular Probes). Sections were then examined using a Zeiss Axiovert or a Leica Confocal microscope.

Example 2

Cervical Cancer

The dual biotherapy as described above was effective in reducing tumor cell number for a variety of cervical cancer cells in vitro A human cervical cancer cell line (SPEC) labeled with luciferase was tested in vivo. $5 \times 10^6$ tumor cells were implanted intraperitoneally into immunodeficient (SCID) mice and allowed to grow for 7 days. Mice were then treated with a single intraperitoneal injection of either PBS, $1 \times 10^7$ CIK cells or $1 \times 10^7$ CIK cells pre-infected with a TK and VGF double deleted vaccinia virus. CIK cells alone transiently delayed the growth of these tumors. Vaccinia virus alone reduced tumor burden, which was followed by relapse in 5 of 7 mice (i.e. 2 of the 7 mice displayed a complete response). The dual biotherapy reduced tumor burden, where 5 of the 7 mice displayed a complete recovery from the tumor.

Example 3

Lung Cancer

A mouse non-small cell lung cancer cell line (CMT 64) was tested in immunocompetent C57B/6 mice. Tumor cells were implanted subcutaneously, and allowed to grow until tumors reached 50-100 mm$^3$. Animals were then treated with a single tail vein injection of either PBS, $1 \times 10^7$ PFU of TK deleted vaccinia virus or $1 \times 10^7$ CIK cells pre-infected with the same vaccinia virus. The dual biotherapy of the invention significantly increased the survival of these mice relative to virus alone (with median survival being 27 days in PBS treated mice; 38 days in virus treated mice and 59 days in dual biotherapy mice). 1 of 7 mice in dual biotherapy group displayed a complete recovery from the tumor, and none in the other treatment groups.

Example 4

Prostate Cancer

In a 3D tissue culture model (spheroid) of the PC3 human prostate cancer cell line, it was seen that infected CIK cells deliver virus to the spheroids and subsequently kill the tumor cells. Spheroids contain 5-10 000 tumor cells and were mixed with CIK cells infected with TK and VGF deleted vaccinia virus, such that there were approximately 10 infected CIK cells/spheroid. By 96 h after addition of the infected CIK cells, the spheroids were completely destroyed.

Example 5

Liver Cancer

The human liver cell lines (HepG2; Hep3B) were cultured in vitro, and shown to be efficiently killed by the dual biotherapy of the invention. Cell monolayers were mixed with CIK cells infected with a TK deleted vaccinia. Little viral infection of the cell layer was seen during the eclipse phase, followed by rapid viral infection of the cell layer (between 48 and 72 h post addition of infected CIK cells), and rapid destruction of the cell layer.

Example 6

Lymphoma

A mouse lymphoma cell line (6780) was grown in immunocompetent animals (FVB) following intraperitoneal injection of $1 \times 10^7$ tumor cells. It was found that subsequent intravenous administration of CIK cells ($1 \times 10^7$ cells) had no effect; virus alone ($1 \times 10^7$ PFU of vaccinia with deletions I the viral TK and VGF genes) briefly reduced tumor burden; and dual biotherapy ($1 \times 10^7$ CIK cells pre-infected with the same virus) reduced tumor burden for an extended period of time.

The dual biotherapy of the invention also prevents relapse, due to both efficient clearance of tumor cells and raising of an anti-tumor immune response. Using a lymphoma cell line (6780) that expresses luciferase, and contains a tetracycline repressible myc oncogene (such that addition of doxycycline to the drinking water of the mice represses the oncogene myc in the cell line, and the tumors regress).

The tumors were grown following intraperitoneal injection and were then regressed by the addition of doxycycline until they were undetectable by bioluminescence imaging. The animals were then treated intravenously with a single injection of PBS; CIK ($1 \times 10^7$ cells); or dual biotherapy ($1 \times 10^7$ CIK cells pre-infected with TK and VGF deleted vaccinia virus), and doxycycline removed from their drinking water.

Figure 8:
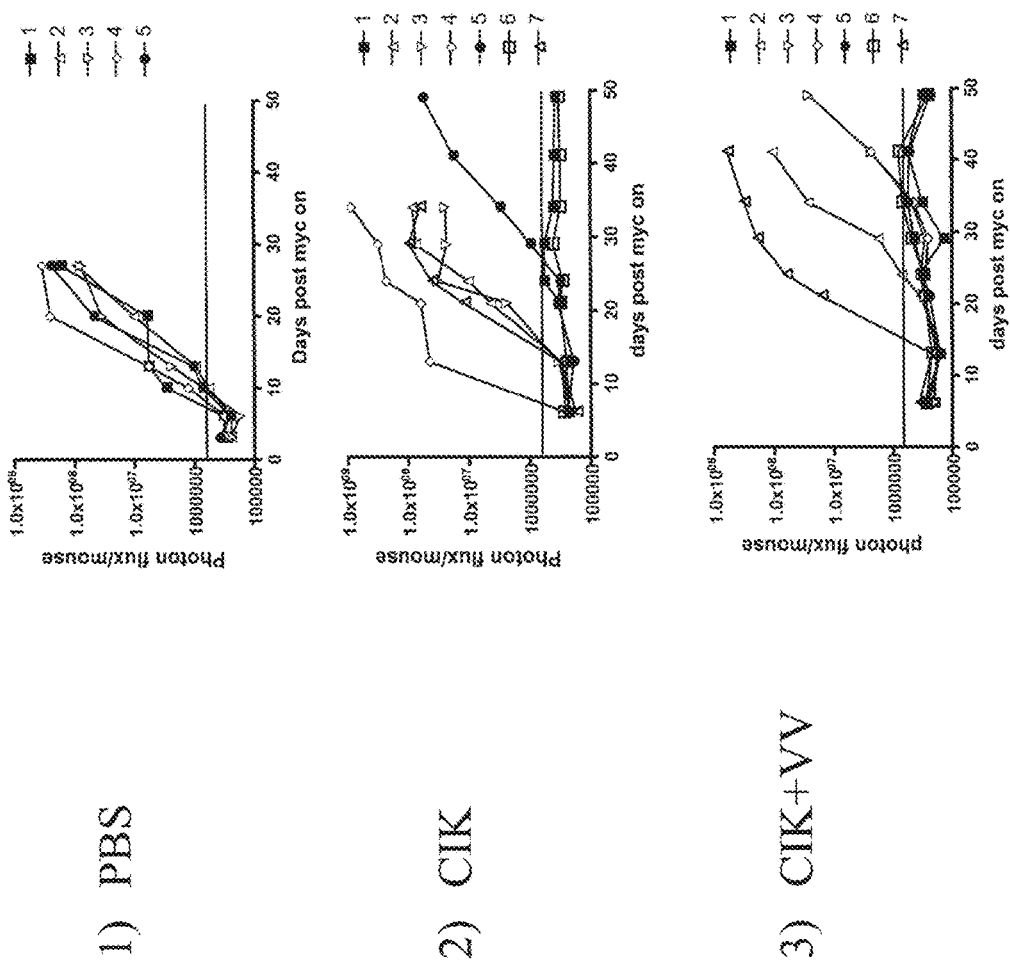
FIG. 8. Graphs depicting the relapse of lymphoma growth in mice treated with PBS alone; CIK cells alone; and CIK cells pre-infected with vaccinia virus.

The control mice all relapsed within 7-10 days. The animals treated with CIK alone had a delay, relapsing from 10 to 90 days after cessation of doxycycline. In the dual biotherapy group, 4 of 7 mice relapsed late (10-90 days), the other 3 mice never relapsed. The data is shown in FIG. 8.

The mice that did not relapse were subsequently challenged with the 6780 lymphoma cells a second time ($1 \times 10^7$ 6780 cells injected intraperitoneally 3 months after the treatment). The mice rejected the tumor cells, and showed an anti-tumor CTL response (splenocytes from these mice were stimulated with 6780 cells in culture and assayed for IFN-gamma production, significantly more splenocytes were activated in these mice than in control mice).

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of treating cancer in a patient, the method comprising:
administering to a cancer patient an effective amount of a mammalian immune effector cell population infected with an oncolytic vaccinia virus, wherein the oncolytic vaccinia virus has a prolonged eclipse period in the immune effector cell population compared to in a tumor cell population, wherein the prolonged eclipse period is not more than about 4 days, and wherein said immune effector cell is a T cell or natural killer (NK) cell and wherein said vaccinia virus comprises a mutation in the viral thymidine kinase (TK) gene and/or the viral growth factor (VGF) gene.

2. The method according to claim 1, wherein said cell population is human.

3. The method according to claim 1, wherein said immune effector cells are expanded in in vitro culture.

4. The method according to claim 3, wherein said effector cell is a cytokine induced killer (CIK) cell.

5. The method according to claim 1, wherein said vaccinia virus comprises a mutation in the viral thymidine kinase gene.

6. The method according to claim 1, wherein said vaccinia virus comprises a mutation in the viral growth factor (VGF) gene.

7. The method according to claim 1, wherein said effector cell is a CD56+ effector cell.

8. The method according to claim 1, wherein said effector cell is a CD3+ CD56+ effector cell.

9. The method according to claim 1, wherein the virus remains in the immune effector cell until the immune effector cell interacts with a tumor in the cancer patient.

10. The method according to claim 1, wherein the immune effector cell is administered to the cancer patient during the eclipse period of the oncolytic virus.

11. The method according to claim 1, wherein the cells are infected with the oncolytic virus at a multiplicity of infection (MOI) of about 1.0 to an MOI of about 10.

12. The method according to claim 1, wherein the oncolytic virus is replication competent.

13. The method according to claim 1, wherein the oncolytic virus is modified.

14. The method according to claim 1, wherein the oncolytic virus comprises a reporter gene.

15. The method according to claim 1, wherein said vaccinia virus comprises mutations of the TK gene and the VGF gene.

16. The method according to claim 1, wherein the immune effector cell is a wherein the vaccinia virus is an EEV virus.

17. The method according to claim 1, wherein the immune effector cells are autologous cells.

18. The method according to claim 1, wherein the immune effector cells are allogeneic cells.

19. The method according to claim 1, wherein the immune effector cell infected with the oncolytic virus is administered by intravascular, subcutaneous, intraperitoneal, or intratumor injection.

20. A method of treating cancer in a patient, the method comprising:
administering to a cancer patient an effective amount of a mammalian T cell population infected with an oncolytic vaccinia virus, wherein the oncolytic vaccinia virus has a prolonged eclipse period in the T cell population compared to in a tumor cell population, wherein the prolonged eclipse period is not more than about 4 days, and wherein said vaccinia virus comprises a mutation in the viral thymidine kinase (TK) gene and/or the viral growth factor (VGF) gene.

21. The method according to claim 20, wherein the T cell is a tumor-infiltrating T cell or a CTL.

22. The method according to claim 20, wherein the T cells are infected with the oncolytic virus at a multiplicity of infection (MOI) of about 1.0 to an MOI of about 10.

23. The method according to claim 20, wherein the T cells are autologous cells.

24. The method according to claim 20, wherein the T cells are allogeneic cells.

25. A method of treating cancer in a patient, the method comprising:
administering to a cancer patient an effective amount of a mammalian natural killer cell population infected with an oncolytic vaccinia virus, wherein the oncolytic vaccinia virus has a prolonged eclipse period in the natural killer cell population compared to in a tumor cell population, wherein the prolonged eclipse period is not more than about 4 days, and wherein said vaccinia virus comprises a mutation in the viral thymidine kinase (TK) gene and/or the viral growth factor (VGF) gene.

26. The method according to claim 25, wherein the NK cell is a LAK cell or a CIK cell.

27. The method according to claim 25, wherein the NK cells are infected with the oncolytic virus at a multiplicity of infection (MOI) of about 1.0 to an MOI of about 10.

28. The method according to claim 25, wherein the NK cells are autologous cells.

29. The method according to claim 25, wherein the NK cells are allogeneic cells.

* * * * *